(12) United States Patent
O'Lenick

(10) Patent No.: US 10,167,414 B1
(45) Date of Patent: Jan. 1, 2019

(54) ALKYL SILICONES AS PIGMENT COATINGS

(71) Applicant: Thomas O'Lenick, Dacula, GA (US)

(72) Inventor: Thomas O'Lenick, Dacula, GA (US)

( * ) Notice: Subject to any disclaimer, the term of this patent is extended or adjusted under 35 U.S.C. 154(b) by 0 days.

(21) Appl. No.: 15/615,949

(22) Filed: Jun. 7, 2017

Related U.S. Application Data

(60) Provisional application No. 62/470,980, filed on Mar. 14, 2016.

(51) Int. Cl.
*C09D 183/06* (2006.01)
*C09D 5/10* (2006.01)
*C09C 3/12* (2006.01)
*C07F 7/08* (2006.01)

(52) U.S. Cl.
CPC .......... *C09D 183/06* (2013.01); *C07F 7/0838* (2013.01); *C09C 3/12* (2013.01); *C09D 5/106* (2013.01)

(58) Field of Classification Search
None
See application file for complete search history.

(56) References Cited

U.S. PATENT DOCUMENTS

| | | | | |
|---|---|---|---|---|
| 4,640,792 A * | 2/1987 | Groenhof | ............... | C08G 77/04 252/573 |
| 4,652,386 A * | 3/1987 | Alberts | ............... | C08G 77/04 508/208 |
| 4,652,624 A * | 3/1987 | Allen | ............... | C08L 83/04 528/17 |
| 4,772,675 A * | 9/1988 | Klosowski | ........... | C08K 5/5415 528/15 |
| 5,331,020 A * | 7/1994 | Brown | ............... | C08G 77/20 427/515 |
| 5,413,781 A * | 5/1995 | Giwa-Agbomeirele | ............... | A61K 8/891 424/401 |
| 5,679,335 A * | 10/1997 | Legrow | ............... | A61K 8/585 424/401 |
| 5,770,187 A * | 6/1998 | Hasebe | ............... | A61K 8/73 424/400 |
| 6,037,434 A * | 3/2000 | De Buyl | ............... | C08G 77/50 528/15 |
| 6,607,631 B1 * | 8/2003 | Badejo | ............... | A61L 24/06 156/325 |
| 7,482,062 B2 * | 1/2009 | Higuchi | ............... | C08G 77/50 428/447 |
| 7,943,720 B2 * | 5/2011 | Tamura | ............... | A61K 8/06 424/401 |
| 2009/0286916 A1 * | 11/2009 | Iwasaki | ............... | C08K 5/5419 524/425 |
| 2012/0301524 A1 * | 11/2012 | Morita | ............... | A61K 8/06 424/401 |
| 2014/0135422 A1 * | 5/2014 | Thorlaksen | ........... | C09D 183/04 523/122 |

* cited by examiner

*Primary Examiner* — Robert S Loewe

(57) ABSTRACT

The present invention is directed to a specific class on pigment reactive silicone polymers that contain both higher alkyl groups and reactive trialkoxy silanes present in the backbone of a specific silicone polymer. By carefully selecting the proper reactive silicone polymer and treating the pigment with said polymer a surprisingly stable and efficient coating is applied the pigment, most importantly ZnO and TiO$_2$ as to render photo stability and alter solubility of the pigment in a variety of solvents.

37 Claims, No Drawings

ALKYL SILICONES AS PIGMENT COATINGS

RELATED APPLICATIONS

This Application claims priority from U.S. provisional application Ser. No. 62/470,980 filed on Mar. 14, 2017, which is hereby incorporated by reference in its entirety.

FIELD OF THE INVENTION

The present invention is directed to a specific class on pigment reactive silicone polymers that contain both higher alkyl groups and reactive trialkoxy silanes present in the backbone of a specific silicone polymer. By carefully selecting the proper reactive silicone polymer and treating the pigment with said polymer a surprisingly stable and efficient coating is applied the pigment, most importantly ZnO and $TiO_2$ as to render photo stability and alter solubility of the pigment in a variety of solvents.

DESCRIPTION OF THE ARTS AND PRACTICES

Zinc oxide is a well known material useful in a variety of applications. It is used as a pigment in paint, as an additive in cosmetic products, cements, glass, rubber, glue, matches, inks and semiconductors. The use of zinc oxide in so many applications areas is a direct result of the many differing properties of the pigment.

Zinc oxide is a reactive material which exhibits a wide range of reactivity with alkaline as well as acidic solutions, liquids and gases. In some applications the reactive nature of the zinc oxide is desirable, for example in paint applications, the reactivity of the pigment results in adhesion into the polymer film. In many applications, it is highly desirable to have zinc oxide in a non-reactive form, that is to eliminate, or make unavailable, the active sites present on the molecule.

Harvey Brown in his book Zinc Oxide Properties and Applications (International Lead Zinc Research Organization) states zinc oxide displays a high degree of reactivity in water with a wide range of materials, including acids, acid salts, and alkaline materials. Many of the resulting compounds are complex structures because of the variety of species furnished by zinc oxide in aqueous solution. Brown goes on to state that zinc oxychloride, zinc phosphates, zinc silicates, and a variety of other materials can be formed in aqueous media. One measure of the availability of reactive groups on the zinc oxide is pH change associated with use of zinc oxide. Zinc oxide containing reactive sites can increase the pH of aqueous products. In some instances the increase can be from an initial pH of 7 to a pH of 8.7. This increase is not only a measure of the presence of reactive groups, but is highly undesirable in the formulation.

It is therefore very desirable to produce a zinc oxide which has the pigment properties but lacks the reactivity found in untreated zinc oxide.

One area in which zinc oxide has been used is in sun screen products. It protects the skin from sun. The traditional materials used for protecting the skin from the harmful effect of the sun are the organic sun screens. These include para amino benzoic acid and other materials which absorb ultra violet light. Recently, studies have indicated that ultra violet light is a major factor in the ageing of skin. This has resulted in the incorporation of sun screens in products which are not aimed specifically for use at the beach, like make up. Additionally, there has been an increased interest in providing higher levels of protection to the skin. The so-called SPF system has been developed to evaluate various materials for their effectiveness in protecting the skin from the damaging effects of the sun. The quest for higher and higher SPF values has resulted in the use of greater levels of organic sun screen. These materials have a tendency to be irritating at high concentrations, and have the affect of increasing the available organic material for bacteria. This results in the need for more preservative to protect the higher level of organic sun screen agent from bacterial degradation. The higher levels of preservative result in higher irritation levels, which can be addressed by incorporation of irritation mitigants, which themselves are degraded by bacteria.

The use of inorganic sun screen agents like zinc oxide is a good way around the use of organic sun screens, since they are not attacked by bacteria. However, their use does have some other inherent problems. Specifically, these materials are not easily formulated into stable products, due to the reactivity issues raised above. Zinc oxide tends to agglomerate in many finished formulations, loosing it's effectiveness in the formulation and resulting in unacceptable aesthetic results, most commonly whitening and viscosity changes. Additionally, zinc oxide tends to raise the pH of the formulation to about 8.5 which is too high for many skin care formulations. These formulations tend to be useful at a pH of 6-7. Zinc oxide has limited usefulness as is due to these problems.

One approach has been to pre-disperse the zinc oxide in an organic oil like Siltech's patented tri-(octyldodecyl) citrate. While the dispersion is fairly stable, the coating is not permanent since there is no reaction between the oil and the zinc oxide. The oil also disrupts the uniformity of the zinc oxide on the skin. Traditionally, dispersing aids have been added to formulations to minimize the disruptive effect upon the film. These include phosphate esters, and lecithin. These too suffer from the labile nature of the surface treatment and dissociation between the particle and the oil. This is especially evident when zinc oxide is exposed to extreme mechanical or thermal stress as in the production of plastics or stick cosmetics.

U.S. Pat. No. 5,486,631 to Mitchnick, et al. issued Jan. 23, 1996 entitled "Silicone polymers for the modification of zinc oxide" discloses a simple alkyl trimethoxy silane s composition and process for hydrophobizing zinc oxide, and the resultant hydrophobic zinc oxide are disclosed. The silicone composition is a reactive alkoxy silicone which is applied to the zinc oxide then in a subsequent step the coated zinc oxide is heated to 40 C to 100 C for between 1 and 10 hours for the reaction to occur. The resulting zinc oxide is hydrophobic, non-reactive, and not affected by water.

The compounds of the Mitchnik patent while an improvement over the use of dispersants the low molecular weight of the polymers and simplicity of the structure:

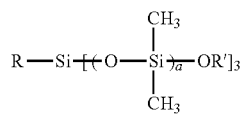

R is alkyl having one to ten carbon atoms;
R' is methyl or ethyl;
a is an integer ranging from 4 to 12.

The structure of the compounds are linear and substituted only at one end with low alkyl and at the other with one trimethoxy group. This means there is only one terminal group that is linked to the Zinc Oxide group. This mechanism is inefficient and results in poor costing uniformity. Additional treatments with the same compounds provide only marginal improvement. It will be understood that the term trimethoxy silane also encompasses triethoxy silane. The only difference is methanol is removed as a by-product of pigment treatment in the former case and ethanol in the latter.

The present invention overcomes the inefficiency problems by making engineered polymers having the proper (1) molecular weight, (2) multiple reactive groups located within the backbone rather than terminal, (3) multiple alkyl groups located within the backbone and (4) a ratio of alkyl to methoxy groups needed to optimize the functionality. None of these shortfalls are addressed in the Mitchnik patent. In fact, Mitchnik teaches away from the present invention leading one of ordinary skill in the art to look for terminal capped trimethoxy compounds. It was not until the process of co-hydrosilylation of alpha olefins and vinyl trimethoxy silane developed that compounds of this type were made available.

THE INVENTION

Object of the Invention

The present invention is directed to a class of pigment reactive silicone compounds having specific (a) alkyl groups present as well as (b) specific triethoxy or trimethoxy groups present, in the proper position on the polymer, and having a specified ratio of (a) to (b).

The present invention is also directed to coated pigments prepared by the reaction of specific pigment reactive silicone polymers with pigments selected from the group consisting of ZnO and TiO$_2$.

SUMMARY OF THE INVENTION

Detailed Description of the Invention

The present invention is directed to a series of pigment reactive silicone polymers having the following structure:

wherein:
a is an integer ranging from 0 to 150;
b is an integer ranging from 1 to 10;
R is independently selected from the groups consisting of:
a) an alkyl having the following structure:

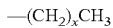

wherein:
x is an integer ranging from 7 to 21;
b) A silane independently selected from the groups having the following structure:
  i. a silane derived from vinyltrimethoxysilane having the structure:

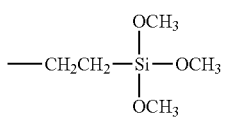

ii. a silane derived from triethoxyvinylsilane having the following structure:

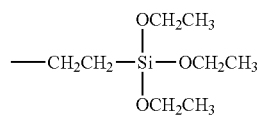

and mixtures thereof:

Another aspect of the present invention is directed to a series of silicone polymers having the following structure:

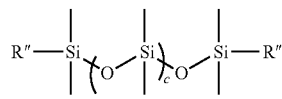

wherein:
c is an integer ranging from 10 to 25;
R" is independently selected from the groups consisting of:
a) an alkyl having the following structure:

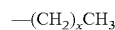

wherein:
x is an integer ranging from 7 to 21;
b) a silane independently selected from the groups having the following structure:
  i. A silane derived from vinyltrimethoxysilane having the structure:

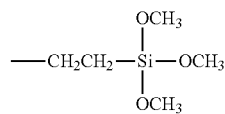

ii. a silane derived from triethoxyvinylsilane having the following structure:

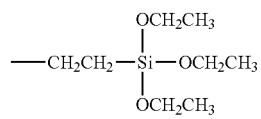

and mixtures thereof:

The present invention also discloses (a) a process for hydrophobizing the surface of zinc oxide with a specific type of reactive silicone, and (b) a novel hydrophobic zinc oxide composition. Additionally, water may be added to the mixture of the reactive silicone and zinc oxide mixture prior to heating. The concentration will be between 1 and 10% water.

It has been found that highly effective system for hydrophobizing zinc oxide makes use of a silicone compound conforming to the following structure:

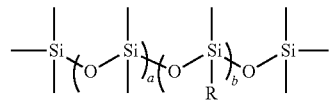

wherein:
a is an integer ranging from 0 to 150;
b is an integer ranging from 1 to 10;
R is independently selected from the groups consisting of:
c) an alkyl having the following structure:

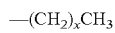

wherein:
x is an integer ranging from 7 to 21;
d) A silane independently selected from the groups having the following structure:
  j. a silane derived from vinyltrimethoxysilane having the structure:

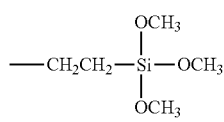

iii. a silane derived from triethoxyvinylsilane having the following structure:

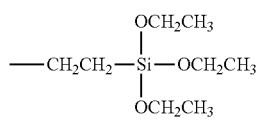

and mixtures thereof:

Another aspect of the present invention is directed to a series of silicone polymers having the following structure:

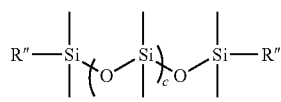

wherein:
c is an integer ranging from 10 to 25;
R" is independently selected from the groups consisting of:
c) an alkyl having the following structure:

wherein:
x is an integer ranging from 7 to 21;
d) a silane independently selected from the groups having the following structure:
  j. A silane derived from vinyltrimethoxysilane having the structure:

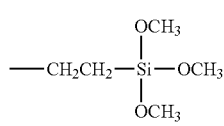

ii. a silane derived from triethoxyvinylsilane having the following structure:

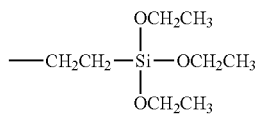

and mixtures thereof.

The zinc hydrophobizing process comprises; contacting zinc oxide with an effective hydrophobizing concentration of a silicone which conforms to the following structure:

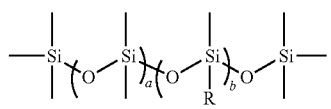

wherein:
a is an integer ranging from 0 to 150;
b is an integer ranging from 1 to 10;
R is independently selected from the groups consisting of:
e) an alkyl having the following structure:

wherein:
x is an integer ranging from 7 to 21;
f) A silane independently selected from the groups having the following structure:
  k. a silane derived from vinyltrimethoxysilane having the structure:

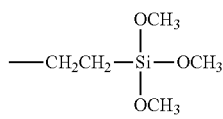

iv. a silane derived from triethoxyvinylsilane having the following structure:

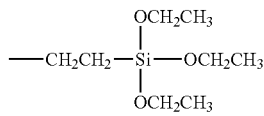

and mixtures thereof:

Another aspect of the present invention is directed to a series of silicone polymers having the following structure:

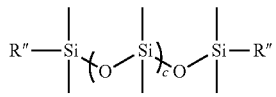

wherein:
c is an integer ranging from 10 to 25;
R" is independently selected from the groups consisting of:
e) an alkyl having the following structure:

wherein:
x is an integer ranging from 7 to 21;

f) a silane independently selected from the groups having the following structure:
k. A silane derived from vinyltrimethoxysilane having the structure:

$$—CH_2CH_2—\underset{\underset{OCH_3}{|}}{\overset{\overset{OCH_3}{|}}{Si}}—OCH_3$$

ii. a silane derived from triethoxyvinylsilane having the following structure:

$$—CH_2CH_2—\underset{\underset{OCH_2CH_3}{|}}{\overset{\overset{OCH_2CH_3}{|}}{Si}}—OCH_2CH_3$$

and mixtures thereof:
then heating the mixture to a temperature of between 40° C. and 100° C., for two to ten hours.

The product so produced surprisingly is hydrophobic and maintains the desirable performance characteristics making the zinc oxide useful in many applications including as a sun screen.

Process

The compounds of the present invention are prepared by contacting zinc oxide with an effective hydrophobizing concentration (generally between 0.1% and 25% by weight of the total formulation) of a silicone which conforms to the following structure:

$$—\underset{|}{\overset{|}{Si}}{\left(O—\underset{|}{\overset{|}{Si}}\right)}_a{\left(O—\underset{\underset{R}{|}}{\overset{|}{Si}}\right)}_b{\left(O—\underset{|}{\overset{|}{Si}}\right)}—$$

wherein:
a is an integer ranging from 0 to 150;
b is an integer ranging from 1 to 10;
R is independently selected from the groups consisting of:
g) an alkyl having the following structure:

$$—(CH_2)_xCH_3$$

wherein:
x is an integer ranging from 7 to 21;
h) A silane independently selected from the groups having the following structure:
1. a silane derived from vinyltrimethoxysilane having the structure:

$$—CH_2CH_2—\underset{\underset{OCH_3}{|}}{\overset{\overset{OCH_3}{|}}{Si}}—OCH_3$$

v. a silane derived from triethoxyvinylsilane having the following structure:

$$—CH_2CH_2—\underset{\underset{OCH_2CH_3}{|}}{\overset{\overset{OCH_2CH_3}{|}}{Si}}—OCH_2CH_3$$

and mixtures thereof:
Another aspect of the present invention is directed to a series of silicone polymers having the following structure:

$$R''—\underset{|}{\overset{|}{Si}}{\left(O—\underset{|}{\overset{|}{Si}}\right)}_c{\left(O—\underset{|}{\overset{|}{Si}}\right)}—R''$$

wherein:
c is an integer ranging from 10 to 25;
R" is independently selected from the groups consisting of:
g) an alkyl having the following structure:

$$—(CH_2)_xCH_3$$

wherein:
x is an integer ranging from 7 to 21;
h) a silane independently selected from the groups having the following structure:
1. A silane derived from vinyltrimethoxysilane having the structure:

$$—CH_2CH_2—\underset{\underset{OCH_3}{|}}{\overset{\overset{OCH_3}{|}}{Si}}—OCH_3$$

ii. a silane derived from triethoxyvinylsilane having the following structure:

$$—CH_2CH_2—\underset{\underset{OCH_2CH_3}{|}}{\overset{\overset{OCH_2CH_3}{|}}{Si}}—OCH_2CH_3$$

and mixtures thereof:
then heating the intermediate to a temperature of between 40° C. and 100° C., for between 2 hr and 10 hr. During this time alcohol is removed. The reaction is considered complete when 97% of the theoretical alcohol is removed. The quantity of alcohol removed is considered more important than the time at which the material is held at temperature.

When R' is —CH$_3$, the alcohol removed is methanol. When R' is —CH$_2$CH$_3$ the alcohol removed is ethanol.

The zinc oxide is coated dry. The silicone can be applied by simply mixing it with the zinc oxide, or in a preferred method using traditional methods for applying liquids to solids like a "V" blender.

Raw Materials

Internal Silicone Hydride

Internal silicone hydrides are commercially available from a variety of sources including Siltech Corporation, Toronto, Ontario, Canada. They have the structure of:

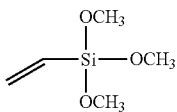

| Example | A | b | Molecular Weight (g/mol) |
|---|---|---|---|
| 1 | 2 | 1 | 370.5 |
| 2 | 150 | 3 | 11,619.4 |
| 3 | 0 | 4 | 404.0 |
| 4 | 8 | 4 | 996.8 |
| 5 | 24 | 8 | 2,583.6 |
| 6 | 20 | 10 | 2,407.4 |
| 7 | 100 | 10 | 8,335.4 |

Terminal Silicone Hydride

Terminal silicone hydrides are commercially available from a variety of sources including Siltech Corporation, Toronto, Ontario, Canada. They have the structure of:

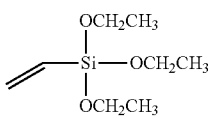

| Example | c | Molecular Weight (g/mol) |
|---|---|---|
| 8 | 10 | 816.1 |
| 9 | 15 | 1,186.6 |
| 10 | 25 | 1,852.5 |

Example 11

Vinyltrimethoxysilane is commercially available from a variety of sources including Sigma-Aldrich and has the following structure:

$$\text{CH}_2=\text{CH}-\text{Si}(\text{OCH}_3)_3$$

C.A.S. number: 2768-02-7

Example 12

Triehoxyvinylsilane is commercially available from a variety of sources including Sigma-Aldrich and has the following structure:

$$\text{CH}_2=\text{CH}-\text{Si}(\text{OCH}_2\text{CH}_3)_3$$

C.A.S. number: 78-08-0

Examples

Alpha-Olefin

Alpha-olefins are hydrocarbons with a primary double bond. They are available from a variety of sources including . . . they have the following structure:

$$\text{CH}_3(\text{CH}_2)_d\text{CH}=\text{CH}_2$$

| Example | d | Molecular Weight (g/mol) |
|---|---|---|
| 13 | 8 | 154.0 |
| 14 | 12 | 210.0 |
| 15 | 16 | 266.0 |
| 16 | 18 | 294.0 |
| 17 | 22 | 350.0 |
| 18 | 26 | 406.0 |

Internal Silane Polymer

| | Silicone Hydride | | Example 11 | Alpha-Olefin | |
|---|---|---|---|---|---|
| Example | Example | Grams | Grams | Example | Grams |
| 19 | 1 | 139.81 | 60.19 | — | — |
| 20 | 2 | 89.98 | 35.22 | 13 | 74.80 |
| 21 | 2 | 82.06 | 48.17 | 14 | 69.77 |
| 22 | 2 | 85.12 | 66.63 | 18 | 48.25 |
| 23 | 3 | 82.11 | 117.89 | — | — |
| 24 | 3 | 77.03 | 82.94 | 14 | 40.04 |
| 25 | 3 | 65.91 | 47.31 | 15 | 86.79 |
| 26 | 3 | 50.53 | 18.14 | 17 | 131.33 |
| 27 | 4 | 126.43 | 73.57 | — | — |
| 28 | 4 | 115.52 | 50.41 | 16 | 34.07 |
| 29 | 4 | 125.01 | 36.37 | 13 | 38.63 |
| 30 | 4 | 102.77 | 14.95 | 15 | 82.28 |
| 31 | 5 | 138.03 | 61.97 | — | — |
| 32 | 5 | 137.70 | 54.10 | 13 | 8.21 |
| 33 | 5 | 129.06 | 28.97 | 14 | 42.96 |
| 34 | 5 | 92.76 | 5.21 | 18 | 102.04 |
| 35 | 6 | 124.35 | 75.65 | — | — |
| 36 | 6 | 122.10 | 66.19 | 14 | 11.72 |
| 37 | 6 | 107.90 | 32.49 | 15 | 59.61 |
| 38 | 6 | 84.43 | 5.09 | 17 | 110.48 |
| 39 | 7 | 170.11 | 29.89 | — | — |
| 40 | 7 | 168.88 | 26.44 | 16 | 4.68 |
| 41 | 7 | 160.44 | 13.96 | 13 | 25.60 |
| 42 | 7 | 143.34 | 2.49 | 15 | 54.17 |

Internal Silane Polymer with Triethoxthyvinylsilane

| | Silicone Hydride | | Example 12 | Alpha-Olefin | |
|---|---|---|---|---|---|
| Example | Example | Grams | Grams | Example | Grams |
| 43 | 1 | 128.60 | 71.40 | — | — |
| 44 | 2 | 85.62 | 43.21 | 13 | 71.17 |
| 45 | 2 | 76.71 | 58.07 | 14 | 65.22 |
| 46 | 2 | 77.63 | 58.07 | 18 | 65.22 |
| 47 | 3 | 70.14 | 129.86 | — | — |
| 48 | 3 | 68.77 | 95.49 | 14 | 35.74 |
| 49 | 3 | 61.68 | 95.49 | 15 | 35.74 |
| 50 | 3 | 49.24 | 22.79 | 17 | 127.97 |
| 51 | 4 | 114.26 | 85.74 | — | — |
| 52 | 4 | 107.66 | 60.59 | 16 | 31.75 |
| 53 | 4 | 118.75 | 44.56 | 13 | 36.69 |
| 54 | 4 | 100.60 | 18.87 | 15 | 80.53 |
| 55 | 5 | 126.66 | 73.34 | — | — |
| 56 | 5 | 127.69 | 64.70 | 13 | 7.61 |
| 57 | 5 | 123.87 | 35.86 | 14 | 40.27 |
| 58 | 5 | 92.06 | 6.66 | 18 | 101.27 |
| 59 | 6 | 112.07 | 87.93 | — | — |
| 60 | 6 | 111.42 | 77.89 | 14 | 10.69 |
| 61 | 6 | 103.05 | 40.02 | 15 | 56.93 |
| 62 | 6 | 83.82 | 6.51 | 17 | 109.67 |
| 63 | 7 | 163.05 | 36.05 | — | — |
| 64 | 7 | 162.65 | 32.84 | 16 | 4.51 |
| 65 | 7 | 157.27 | 17.64 | 13 | 25.09 |
| 66 | 7 | 142.82 | 3.20 | 15 | 53.97 |

Mixed alkyl Silane polymer

| | Silicone Hydride | | Siloxane | | Alpha-Olefin | | | |
|---|---|---|---|---|---|---|---|---|
| Example | Example | Grams | Example | Grams | Example | Grams | Example | Grams |
| 67 | 2 | 80.41 | 12 | 40.59 | 13 | 33.42 | 14 | 45.58 |
| 68 | 3 | 56.46 | 12 | 26.14 | 15 | 55.77 | 16 | 61.64 |
| 69 | 4 | 110.16 | 12 | 62.00 | 13 | 8.51 | 17 | 19.34 |
| 70 | 5 | 119.07 | 12 | 34.47 | 13 | 14.19 | 17 | 32.26 |
| 71 | 6 | 102.76 | 12 | 15.96 | 14 | 35.86 | 15 | 45.42 |
| 72 | 7 | 146.27 | 12 | 6.56 | 15 | 18.67 | 18 | 28.50 |
| 73 | 2 | 84.25 | 11 | 32.97 | 13 | 35.02 | 14 | 47.75 |
| 74 | 3 | 58.17 | 11 | 20.88 | 15 | 57.45 | 16 | 63.50 |
| 75 | 4 | 118.40 | 11 | 51.67 | 13 | 9.15 | 17 | 20.79 |
| 76 | 5 | 123.87 | 11 | 27.81 | 13 | 14.77 | 17 | 33.56 |
| 77 | 6 | 104.64 | 11 | 12.60 | 14 | 36.51 | 15 | 46.25 |
| 78 | 7 | 147.35 | 11 | 5.13 | 15 | 18.81 | 18 | 28.71 |

Terminal Silane Polymer

| | Silicone Hydride | | Silane | | Alpha-Olefin | |
|---|---|---|---|---|---|---|
| Example | Example | Grams | Example | Grams | Example | Grams |
| 79 | 8 | 145.65 | 11 | 54.35 | — | — |
| 80 | 8 | 135.03 | 12 | 64.97 | — | — |
| 81 | 9 | 159.16 | 11 | 49.73 | — | — |
| 82 | 9 | 150.27 | 12 | 28.23 | — | — |
| 83 | 10 | 171.77 | 11 | 28.23 | — | — |
| 84 | 10 | 165.02 | 12 | 34.98 | — | — |
| 85 | 8 | 144.49 | 11 | 28.24 | 13 | 27.27 |
| 86 | 8 | 138.82 | 12 | 34.99 | 13 | 26.19 |
| 87 | 8 | 137.67 | 11 | 26.91 | 14 | 35.43 |
| 88 | 8 | 132.51 | 12 | 33.40 | 14 | 34.10 |
| 89 | 8 | 131.46 | 11 | 25.69 | 15 | 42.85 |
| 90 | 8 | 118.73 | 12 | 42.57 | 15 | 38.70 |
| 91 | 8 | 128.56 | 11 | 25.13 | 16 | 46.31 |
| 92 | 8 | 116.36 | 12 | 41.72 | 16 | 41.92 |
| 93 | 8 | 123.13 | 11 | 24.06 | 17 | 52.81 |
| 94 | 8 | 111.89 | 12 | 40.12 | 17 | 47.99 |
| 95 | 8 | 118.14 | 11 | 23.09 | 18 | 58.77 |
| 96 | 8 | 107.76 | 12 | 38.63 | 18 | 53.61 |
| 97 | 9 | 158.20 | 11 | 21.27 | 13 | 20.53 |
| 98 | 9 | 153.48 | 12 | 26.61 | 13 | 19.92 |
| 99 | 9 | 152.51 | 11 | 20.50 | 14 | 26.99 |
| 100 | 9 | 148.11 | 12 | 25.68 | 14 | 26.21 |
| 101 | 9 | 147.21 | 11 | 19.79 | 15 | 33.00 |
| 102 | 9 | 135.98 | 12 | 33.53 | 15 | 30.48 |
| 103 | 9 | 144.70 | 11 | 19.45 | 16 | 35.85 |
| 104 | 9 | 133.84 | 12 | 33.00 | 16 | 33.16 |
| 105 | 9 | 139.92 | 11 | 18.81 | 17 | 41.27 |
| 106 | 9 | 129.74 | 12 | 31.99 | 17 | 38.27 |
| 107 | 9 | 135.45 | 11 | 18.21 | 18 | 46.34 |
| 108 | 9 | 125.89 | 12 | 31.04 | 18 | 43.07 |
| 109 | 10 | 171.05 | 11 | 14.73 | 13 | 14.22 |
| 110 | 10 | 167.48 | 12 | 18.60 | 13 | 13.92 |
| 111 | 10 | 166.74 | 11 | 14.36 | 14 | 18.90 |
| 112 | 10 | 163.35 | 12 | 18.14 | 14 | 18.52 |
| 113 | 10 | 162.64 | 11 | 14.00 | 15 | 23.35 |
| 114 | 10 | 153.66 | 12 | 24.27 | 15 | 22.06 |
| 115 | 10 | 160.67 | 11 | 13.83 | 16 | 25.50 |
| 116 | 10 | 151.90 | 12 | 23.99 | 16 | 24.11 |
| 117 | 10 | 156.86 | 11 | 13.51 | 17 | 29.64 |
| 118 | 10 | 148.49 | 12 | 23.45 | 17 | 28.05 |
| 119 | 10 | 153.23 | 11 | 13.19 | 18 | 33.58 |
| 120 | 10 | 145.23 | 12 | 22.94 | 18 | 31.83 |

Preparation of the Pigment Reactive silicone Polymers of the Present Invention

Vinyl Trimethoxyl Silane

| Example | Example | Grams | ZnO |
|---|---|---|---|
| 121 | 19 | 1.0 | 99.0 |
| 122 | 20 | 2.0 | 98.0 |
| 123 | 21 | 1.0 | 99.0 |
| 124 | 22 | 2.0 | 98.0 |
| 125 | 23 | 1.0 | 99.0 |
| 126 | 24 | 2.0 | 98.0 |
| 127 | 25 | 1.0 | 99.0 |
| 128 | 26 | 2.0 | 98.0 |
| 129 | 27 | 1.0 | 99.0 |
| 130 | 28 | 2.0 | 98.0 |
| 131 | 29 | 1.0 | 99.0 |
| 132 | 30 | 2.0 | 98.0 |
| 133 | 31 | 1.0 | 99.0 |
| 134 | 32 | 2.0 | 98.0 |
| 135 | 33 | 1.0 | 99.0 |
| 136 | 34 | 2.0 | 98.0 |
| 137 | 35 | 1.0 | 99.0 |
| 138 | 36 | 2.0 | 98.0 |
| 139 | 37 | 1.0 | 99.0 |
| 140 | 38 | 2.0 | 98.0 |
| 141 | 39 | 1.0 | 99.0 |
| 142 | 40 | 2.0 | 98.0 |
| 143 | 41 | 1.0 | 99.0 |
| 144 | 42 | 2.0 | 98.0 |
| 145 | 43 | 1.0 | 99.0 |
| 146 | 44 | 2.0 | 98.0 |
| 147 | 45 | 1.0 | 99.0 |
| 148 | 46 | 2.0 | 98.0 |
| 149 | 47 | 1.0 | 99.0 |
| 150 | 48 | 2.0 | 98.0 |
| 151 | 49 | 1.0 | 99.0 |
| 152 | 50 | 2.0 | 98.0 |
| 153 | 51 | 1.0 | 99.0 |
| 154 | 52 | 2.0 | 98.0 |
| 155 | 53 | 1.0 | 99.0 |
| 156 | 54 | 2.0 | 98.0 |
| 157 | 55 | 1.0 | 99.0 |
| 158 | 56 | 2.0 | 98.0 |
| 159 | 57 | 1.0 | 99.0 |
| 160 | 58 | 2.0 | 98.0 |
| 161 | 59 | 1.0 | 99.0 |
| 162 | 60 | 2.0 | 98.0 |
| 163 | 61 | 1.0 | 99.0 |
| 164 | 62 | 2.0 | 98.0 |
| 165 | 63 | 1.0 | 99.0 |
| 166 | 64 | 2.0 | 98.0 |
| 167 | 65 | 1.0 | 99.0 |
| 168 | 66 | 2.0 | 98.0 |
| 169 | 67 | 1.0 | 99.0 |
| 170 | 68 | 2.0 | 98.0 |
| 171 | 69 | 1.0 | 99.0 |
| 172 | 70 | 2.0 | 98.0 |
| 173 | 71 | 1.0 | 99.0 |
| 174 | 72 | 2.0 | 98.0 |
| 175 | 73 | 1.0 | 99.0 |
| 176 | 74 | 2.0 | 98.0 |
| 177 | 75 | 1.0 | 99.0 |
| 178 | 76 | 2.0 | 98.0 |
| 179 | 77 | 1.0 | 99.0 |
| 180 | 78 | 2.0 | 98.0 |
| 181 | 79 | 1.0 | 99.0 |
| 182 | 80 | 2.0 | 98.0 |
| 182 | 81 | 1.0 | 99.0 |
| 183 | 82 | 2.0 | 98.0 |
| 184 | 83 | 1.0 | 99.0 |
| 185 | 84 | 2.0 | 98.0 |
| 186 | 85 | 1.0 | 99.0 |
| 187 | 86 | 2.0 | 98.0 |
| 188 | 87 | 1.0 | 99.0 |
| 189 | 88 | 2.0 | 98.0 |
| 190 | 89 | 1.0 | 99.0 |
| 191 | 90 | 2.0 | 98.0 |
| 192 | 91 | 1.0 | 99.0 |
| 192 | 92 | 2.0 | 98.0 |

-continued

Preparation of the Pigment Reactive silicone
Polymers of the Present Invention

Vinyl Trimethoxyl Silane

| Example | Example | Grams | ZnO |
|---|---|---|---|
| 193 | 93 | 1.0 | 99.0 |
| 194 | 94 | 2.0 | 98.0 |
| 195 | 95 | 1.0 | 99.0 |
| 196 | 96 | 2.0 | 98.0 |
| 197 | 97 | 1.0 | 99.0 |
| 198 | 98 | 2.0 | 98.0 |
| 199 | 99 | 1.0 | 99.0 |
| 200 | 100 | 2.0 | 98.0 |
| 201 | 101 | 1.0 | 99.0 |
| 202 | 102 | 2.0 | 98.0 |
| 203 | 103 | 1.0 | 99.0 |
| 204 | 104 | 2.0 | 98.0 |
| 205 | 105 | 1.0 | 99.0 |
| 206 | 106 | 2.0 | 98.0 |
| 207 | 107 | 1.0 | 99.0 |
| 208 | 108 | 2.0 | 98.0 |
| 209 | 109 | 1.0 | 99.0 |
| 210 | 110 | 2.0 | 98.0 |
| 211 | 111 | 2.0 | 98.0 |
| 212 | 112 | 1.0 | 99.0 |
| 213 | 113 | 2.0 | 98.0 |
| 214 | 114 | 1.0 | 99.0 |
| 215 | 115 | 2.0 | 98.0 |
| 216 | 116 | 1.0 | 99.0 |
| 217 | 117 | 2.0 | 98.0 |
| 218 | 118 | 1.0 | 99.0 |
| 219 | 119 | 2.0 | 98.0 |
| 220 | 120 | 1.0 | 99.0 |

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

What is claimed:

1. A reactive silicone polymer having the following structure:

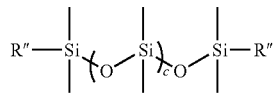

wherein:
c is an integer ranging from 10 to 25;
R″ is a mixture of:
a) an alkyl having the following structure:

—(CH$_2$)$_x$CH$_3$ wherein:
x is an integer ranging from 7 to 21;
and
b) a silane having a structure selected from the group consisting of
 i. —CH$_2$CH$_2$Si(OCH$_3$)$_3$
 ii. —CH$_2$CH$_2$Si(OCH$_2$CH$_3$)$_3$.

2. The reactive silicone of claim 1 where

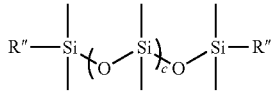

wherein:
c is 10;
R″ is a mixture of —CH$_2$CH$_2$Si(OCH$_3$)$_3$ and alkyl wherein x is 7.

3. The reactive silicone of claim 1 where in

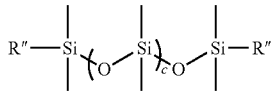

wherein:
c is 25;
R″ is a mixture of —CH$_2$CH$_2$Si(OCH$_3$)$_3$ and alkyl wherein x is 7.

4. The reactive silicone of claim 1 where in

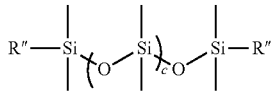

wherein:
c is 10;
R″ is a mixture of —CH$_2$CH$_2$Si(OCH$_3$)$_3$ and alkyl having 22 carbon atoms.

5. The reactive silicone of claim 1 where in

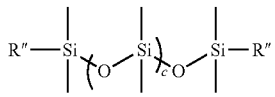

wherein:
c is 25;
R″ is a mixture of —CH$_2$CH$_2$Si(OCH$_3$)$_3$ and alkyl having 22 carbon atoms.

6. The reactive silicone of claim 1 where in

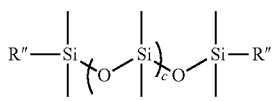

wherein:
c is 10;
R″ is a mixture of —CH$_2$CH$_2$Si(OCH$_2$CH$_3$)$_3$ and alkyl wherein x is 7.

7. The reactive silicone of claim 1 where in

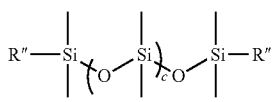

wherein:
c is 25;
R" is a mixture of —CH$_2$CH$_2$Si(OCH$_2$CH$_3$)$_3$ and alkyl wherein x is 7.

8. The reactive silicone of claim 1 where in

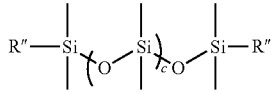

wherein:
c is 10;
R" is a mixture of —CH$_2$CH$_2$Si(OCH$_2$CH$_3$)$_3$ and alkyl having 22 carbon atoms.

9. The reactive silicone of claim 1 where in

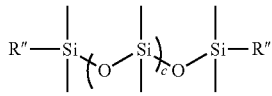

wherein:
c is 25;
R" is a mixture of —CH$_2$CH$_2$Si(OCH$_2$CH$_3$)$_3$ and alkyl having 22 carbon atoms.

10. The reactive silicone of claim 1 where in

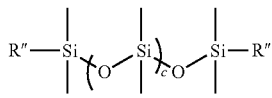

wherein:
c is 10;
R" is a mixture of —CH$_2$CH$_2$Si(OCH$_3$)$_3$ and alkyl wherein x is 15.

11. The reactive silicone of claim 1 where in

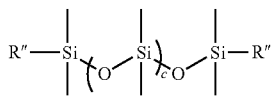

wherein:
c is 25;
R" is a mixture of —CH$_2$CH$_2$Si(OCH$_3$)$_3$ and alkyl wherein x is 15.

12. The reactive silicone of claim 1 where in

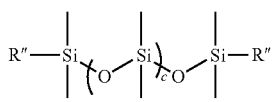

wherein:
c is 10;
R" is a mixture of —CH$_2$CH$_2$Si(OCH$_3$)$_3$ and alkyl having 15 carbon atoms.

13. The reactive silicone of claim 1 where in

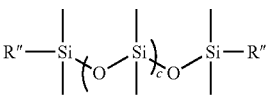

wherein:
c is 25;
R" is a mixture of —CH$_2$CH$_2$Si(OCH$_3$)$_3$ and alkyl having 15 carbon atoms.

14. The reactive silicone of claim 1 where in

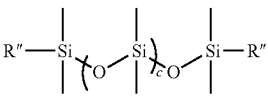

wherein:
c is 10;
R" is a mixture of —CH$_2$CH$_2$Si(OCH$_2$CH$_3$)$_3$ and alkyl wherein x is 15.

15. The reactive silicone of claim 1 where in

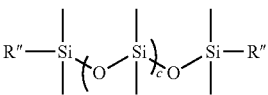

wherein:
c is 25;
R" is a mixture of —CH$_2$CH$_2$Si(OCH$_2$CH$_3$)$_3$ and alkyl wherein x is 15.

16. The reactive silicone of claim 1 where in

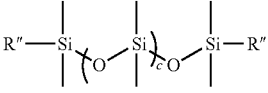

wherein:
c is 10;
R" is a mixture of —CH$_2$CH$_2$Si(OCH$_2$CH$_3$)$_3$ and alkyl having 15 carbon atoms.

17. The reactive silicone of claim 1 where in

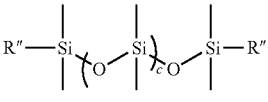

wherein:
c is 25;
R" is a mixture of —CH$_2$CH$_2$Si(OCH$_2$CH$_3$)$_3$ and alkyl having 15 carbon atoms.

18. A process for coating zinc oxide with the reactive silicone of claim 1 which comprises:
  i. mixing the reactive silicone and zinc oxide together;
  ii. heating the mixture to a temperature of between 40° C. and 100° C.;
  iii. holding the temperature of said mixture for two to ten hours, generating methanol or ethanol.

19. A reactive silicone polymer composition the following structure:

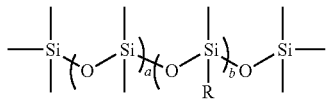

wherein:
a is an integer ranging from 0 to 150;
b is an integer ranging from 1 to 10;
R is a mixture of:
  a) an alkyl having the following structure:

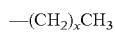

wherein:
  x is an integer ranging from 7 to 21;
  and
  b) A silane having a structure selected from the groups consisting of:
  i. 
  ii. 

20. The reactive silicone of claim 19 wherein:
a is 2;
b is 1;
R is a mixture of —$CH_2CH_2Si(OCH_3)_3$ and alkyl wherein x is 7.

21. The reactive silicone of claim 19 wherein:
a is 2;
b is 1;
R is a mixture of —$CH_2CH_2Si(OCH_2CH_3)_3$ and alkyl wherein x is 7.

22. The reactive silicone of claim 19 wherein:
a is 2;
b is 1;
R is a mixture of —$CH_2CH_2Si(OCH_3)_3$ and alkyl wherein x is 15.

23. The reactive silicone of claim 19 wherein:
a is 2;
b is 1;
R is a mixture of —$CH_2CH_2Si(OCH_2CH_3)_3$ and alkyl wherein x is 15.

24. The reactive silicone of claim 19 wherein:
a is 2;
b is 1;
R is a mixture of —$CH_2CH_2Si(OCH_3)_3$ and alkyl wherein x is 21.

25. The reactive silicone of claim 19 wherein:
a is 2;
b is 1;
R is a mixture of —$CH_2CH_2Si(OCH_2CH_3)_3$ and alkyl wherein x is 21.

26. The reactive silicone of claim 19 wherein:
a is 20;
b is 10;
R is a mixture of —$CH_2CH_2Si(OCH_3)_3$ and alkyl wherein x is 7.

27. The reactive silicone of claim 19 wherein:
a is 20;
b is 10;
R is a mixture of —$CH_2CH_2Si(OCH_2CH_3)_3$ and alkyl wherein x is 7.

28. The reactive silicone of claim 19 wherein:
a is 20;
b is 10;
R is a mixture of —$CH_2CH_2Si(OCH_3)_3$ and alkyl wherein x is 15.

29. The reactive silicone of claim 19 wherein:
a is 20;
b is 10;
R is a mixture of —$CH_2CH_2Si(OCH_2CH_3)_3$ and alkyl wherein x is 15.

30. The reactive silicone of claim 19 wherein:
a is 20;
b is 10;
R is a mixture of —$CH_2CH_2Si(OCH_3)_3$ and alkyl wherein x is 21.

31. The reactive silicone of claim 19 wherein:
a is 20;
b is 10;
R is a mixture of —$CH_2CH_2Si(OCH_2CH_3)_3$ and alkyl wherein x is 21.

32. The reactive silicone of claim 19 wherein:
a is 150;
b is 3;
R is a mixture of —$CH_2CH_2Si(OCH_3)_3$ and alkyl wherein x is 7.

33. The reactive silicone of claim 19 wherein:
a is 150;
b is 3;
R is a mixture of —$CH_2CH_2Si(OCH_2CH_3)_3$ and alkyl wherein x is 7.

34. The reactive silicone of claim 19 wherein:
a is 150;
b is 3;
R is a mixture of —$CH_2CH_2Si(OCH_3)_3$ and alkyl wherein x is 15.

35. The reactive silicone of claim 19 wherein:
a is 150;
b is 3;
R is a mixture of —$CH_2CH_2Si(OCH_2CH_3)_3$ and alkyl wherein x is 15.

36. The reactive silicone of claim 19 wherein:
a is 150;
b is 3;
R is a mixture of —$CH_2CH_2Si(OCH_3)_3$ and alkyl wherein x is 21.

37. The process for coating zinc oxide with the reactive silicone of claim 19 comprises:
  iv. mixing the reactive silicone and zinc oxide together;
  v. heating the mixture to a temperature of between 40° C. and 100° C.;
  vi. holding the temperature of said mixture for two to ten hours, generating methanol or ethanol.

* * * * *